United States Patent
Scheying et al.

(10) Patent No.: US 7,553,402 B2
(45) Date of Patent: Jun. 30, 2009

(54) METHOD AND DEVICE FOR DEVELOPING AN ELECTROCHEMICAL MEASURING SYSTEM

(75) Inventors: Gerd Scheying, Stuttgart (DE); Thomas Brinz, Bissingen A.D. Teck (DE)

(73) Assignee: Robert Bosch GmbH, Stuttgart (DE)

( * ) Notice: Subject to any disclaimer, the term of this patent is extended or adjusted under 35 U.S.C. 154(b) by 799 days.

(21) Appl. No.: 10/847,138

(22) Filed: May 17, 2004

(65) Prior Publication Data
US 2004/0262151 A1 Dec. 30, 2004

(30) Foreign Application Priority Data
May 26, 2003 (DE) ............... 103 23 638

(51) Int. Cl.
*G01N 27/403* (2006.01)
(52) U.S. Cl. .............. 205/775; 205/787.5; 204/400; 204/412
(58) Field of Classification Search ........ 205/775, 205/787.5; 204/400, 412, 433
See application file for complete search history.

(56) References Cited

U.S. PATENT DOCUMENTS

| | | | | |
|---|---|---|---|---|
| 3,484,359 A | * | 12/1969 | Brown et al. | 204/400 |
| 4,211,623 A | * | 7/1980 | Ross et al. | 204/419 |
| 4,457,161 A | | 7/1984 | Iwanaga et al. | |
| 4,496,454 A | * | 1/1985 | Berger | 204/402 |
| 5,378,343 A | | 1/1995 | Kounaves et al. | |
| 5,389,215 A | * | 2/1995 | Horiuchi et al. | 205/775 |
| 6,187,164 B1 | * | 2/2001 | Warren et al. | 205/81 |
| 6,773,563 B2 | * | 8/2004 | Matsumoto | 204/401 |

FOREIGN PATENT DOCUMENTS

| | | |
|---|---|---|
| DE | 42 36 421 | 5/1994 |
| DE | 42 44 338 | 7/1994 |
| DE | 101 02 657 | 1/2003 |
| EP | 0 366 795 | 5/1990 |
| GB | 2 318 874 | 5/1998 |

OTHER PUBLICATIONS

Sullivan et al, Analytical Chemistry, Oct. 1999, 71(19), pp. 4369-4375.*
Orion, 1997 Laboratory Products and Electrochemistry Handbook, pp. 78-81.*

* cited by examiner

*Primary Examiner*—Kaj K Olsen
(74) *Attorney, Agent, or Firm*—Kenyon & Kenyon LLP

(57) ABSTRACT

A method and a device for developing an electrochemical measuring system, in particular a sensor, is provided. A plurality of different electrode materials are applied to at least one substrate and introduced into a medium together with at least one reference electrode. Subsequently, the electrochemical potentials of the individual electrode materials in relation to the reference electrode are determined.

12 Claims, 2 Drawing Sheets

METHOD AND DEVICE FOR DEVELOPING AN ELECTROCHEMICAL MEASURING SYSTEM

FIELD OF THE INVENTION

The present invention relates to a method and a device for developing an electrochemical measuring system, e.g., a sensor.

BACKGROUND INFORMATION

Electrochemical measuring systems, e.g., sensors, are used customarily, for example, to determine a pH value of a liquid medium or also to determine a carbon dioxide concentration of a medium. Measuring systems configured for such purposes include potentiometric electrodes that may be configured in a variety of manners. To determine a pH, for example, a pH-sensitive glass electrode and a reference electrode are used. To determine a carbon dioxide concentration, for example, a platinum electrode is used in combination with a silver reference electrode.

Potentiometric electrodes are classified as ion electrodes or redox electrodes. Ion electrodes are in turn classified as type 1 ion electrodes or type 2 ion electrodes. In the case of a type 1 ion electrode, the metal making up the electrode is submerged into a solution of its own salt. An electrode of this type is, for example, an $Ag/AgNO_3$ electrode. In the case of an ion electrode of the second type, a metal coated with a poorly soluble metal salt is submerged into an aqueous solution containing a readily soluble, chemically inert salt including the same anion as the metal salt.

A redox electrode is made up of a neutral working electrode, which is made, for example, of platinum, and a solution containing a corresponding redox pair.

An electrode of the second type is used, for example, as a reference electrode, because it allows uncomplicated handling when the potential signal is constant.

To develop an electrochemical measuring system including one electrode, various materials are tested individually and in succession in relation to a suitable reference electrode for the selection of the electrode material. This method for selecting an electrode material has the disadvantage of being very time-consuming.

SUMMARY OF THE INVENTION

The method of the present invention provides for testing of a plurality of electrode materials for selecting an electrode for an electrochemical measuring system, without requiring a laborious change of the electrode materials or of the medium. In particular, the method of the present invention facilitates a highly time-efficient process for determining an electrode material suitable for an electrochemical measuring system. The fact that a plurality of electrode materials are applied to the substrate allows testing of numerous electrode combinations in one operation. The method of the present invention allows a fast and direct comparison of different electrode materials because the required measurements, i.e., the determination of the electrochemical potential, may be performed within a short period of time and in the same medium.

It is also possible that in the implementation of the method, a plurality of substrates, to which one or a plurality of electrode materials are applied, are inserted into the medium and the individual electrode materials are then tested in relation to the at least one reference electrode.

Electrochemical measuring systems that are intended for use under unusual measuring conditions may be optimized using the method of the present invention. It is thus possible, for example, using the method of the present invention, to optimize electrodes of potentiometric sensors that are intended for use in media such as oils, fuels or the like. In these media, the chemical processes occurring are occasionally complex or even unknown from time to time.

The substrate may be an electrical insulator made, for example, from a material such as aluminum oxide, silicon or glass.

The individual electrode materials may be coated with one electrolyte each for the development of a type 2 electrode. For example, silver, which is used as an electrode material, may be provided with a silver chloride coating. Individual arrays of the same electrode material may also be coated with different electrolytes. This may allow screening of electrode combinations, electrolyte materials and electrolyte-electrode combinations simultaneously.

The electrode materials are applied to the substrate using a suitable method, for example, a sputtering method, chemical vapor deposition (CVD), a galvanic method, a dispensing method, or even a suitable printing method.

In order to miniaturize the substrate and the electrode materials arranged on it, the latter are, for example, applied to the substrate using a lithographic method. The electrolytes may also be applied to the electrode materials by suitable methods. This may allow analysis of the individual electrode materials in a small measuring vessel and using small quantities of the medium.

The individual electrode materials are provided with a lead, to which a measuring device is connected. The individual leads may be insulated from each other by insulation layers, bridgings and/or back bondings.

Cross-over circuits or the like may allow for measurement of various electrode combinations using a bonding.

The measuring device includes, for example, a multiplexer, which allows activation of the different electrode materials, thus allowing variation of the electrode materials in parallel or sequentially in relation to the at least one fixed reference electrode.

Also, in accordance with the present invention, a device for developing at least one electrochemical measuring system includes a potentiometric electrode. This device includes: at least one substrate onto which a plurality of different electrode materials are applied; at least one reference electrode; a measuring vessel in which the substrate and the reference electrode are arranged; and a measuring device via which it is possible to measure the electrochemical potential of the individual electrode materials in relation to the at least one reference electrode.

The substrate is configured, for example, in the shape of a plate or cylinder.

In order to be able to test different electrode combinations, the device according to the present invention may also include a motion device, which is in the form of, for example, an electric motor, which makes it possible to move the electrode materials and the reference electrode in relation to each other.

Furthermore, the device of the present invention may include a spacer, which determines the spacing between the reference electrode and the electrode material placed in a measuring position. The spacer ensures that the measuring conditions are identical when different electrode combinations are tested. The spacer is made, for example from a plastic film, which is arranged in the areas of the substrate that are free from electrode materials. Thus, when two substrates including different electrode materials are used, the electrode materials of one substrate are in contact with the film forming the other substrate.

DETAILED DESCRIPTION

Figure 1:
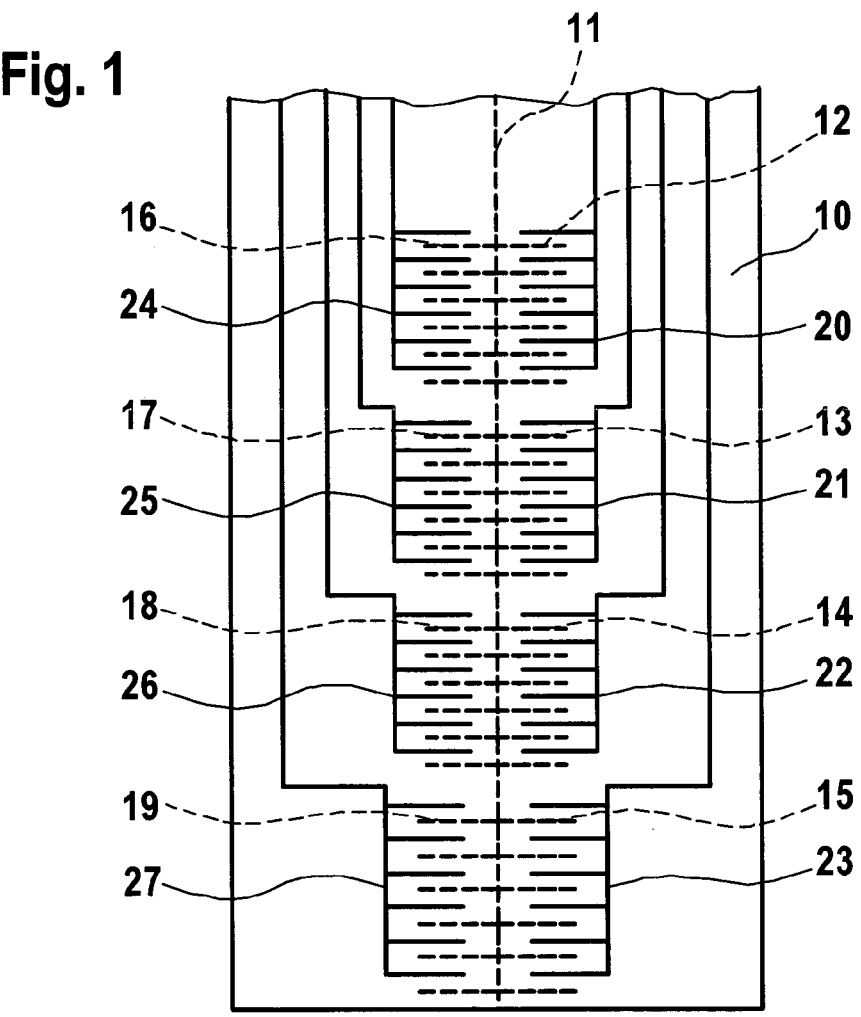
FIG. 1 shows a system of a plurality of electrode materials and one reference electrode on a substrate.

FIG. 1 shows a substrate 10, using which it is possible to develop an electrode combination for a potentiometric sensor and which is made from an electrical insulator such as aluminum oxide.

A reference electrode 11 is applied to substrate 10, the reference electrode including eight comb-like areas 12 through 19. Comb-like electrode areas 12 through 19 interact with similarly comb-like working electrodes and counter-electrodes 20, 21, 22, 23, 24, 25, 26 and 27, respectively. The reference electrode is a silver/silver bromide electrode. Counter-electrode 20 is made from platinum, counter-electrode 21 is made from palladium, counter-electrode 22 is made from copper, counter-electrode 23 is made from cobalt, counter-electrode 24 is made from nickel, counter-electrode 25 is made from iridium, counter-electrode 26 is made from rhodium and counter-electrode 27 is made from gold. Each of individual counter-electrodes 20 through 27 includes a separate lead.

In order to manufacture the measuring system shown in FIG. 1, silver is first sputtered onto substrate 10 to form reference electrode 11. Platinum, palladium, copper, cobalt, nickel, iridium, rhodium and gold are then sputtered onto substrate 10 to produce counter-electrodes 20 through 27. The silver applied to form reference electrode 11 is then bonded. Substrate 10 is then submerged together with an external platinum electrode into a bath of 5% potassium bromide solution. A current is applied to the surface of the silver in such a manner that the silver surface is converted into silver bromide. This results in the production of a silver/silver bromide reference electrode. This electrode is a type 2 electrode.

Subsequently, reference electrode 11 and counter-electrodes 20 through 27 are bonded and submerged into a measuring liquid, which is arranged in a measuring vessel. Using a measuring device, which includes a multiplexer and a high-resistivity measuring instrument, counter-electrodes 20 through 27 are now switched to oppose reference electrode 11, the potential applied in each case being measured using the high-resitivity measuring device.

Furthermore, the concentration of an analyte contained in the measuring liquid may be varied so that a correlation of the measured potential in relation to the concentration of the analyte may be used to determine the best electrode combination for the application in question.

It is also conceivable that more than eight counter-electrodes, for example, 30 counter-electrodes, and a corresponding number of reference electrodes are arranged on substrate 10, it being possible to switch or measure the reference electrodes potentiometrically in relation to the 30 counter-electrodes using a multiplexer.

Figure 2:
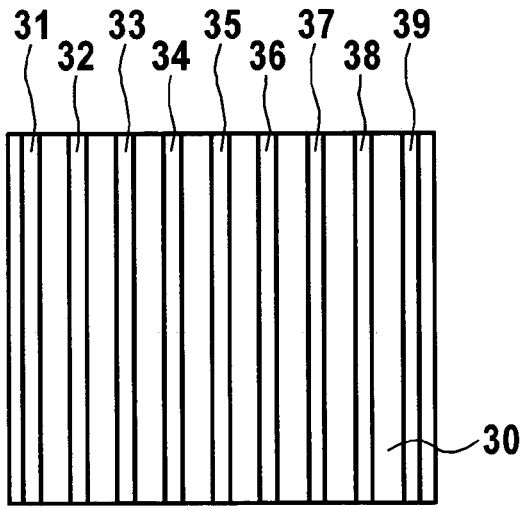
FIG. 2 shows an alternative system of a plurality of electrode materials on a substrate.
Figure 3:
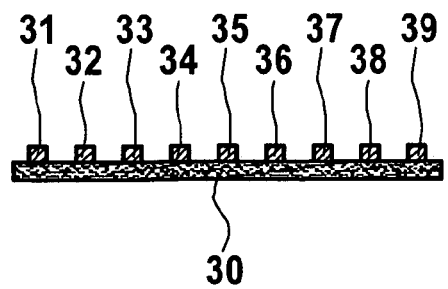
FIG. 3 shows a cross-section taken through the system shown in FIG. 2.

FIGS. 2 and 3 show a substrate 30 made from an electrical insulator used for the development of an electrochemical sensor, nine electrodes 31 through 39 made of different materials being applied in strips to substrate 30. Electrode materials 31 through 39 may be connected to a measuring instrument, via a through hole leading to the back of substrate 30.

Figure 4A:
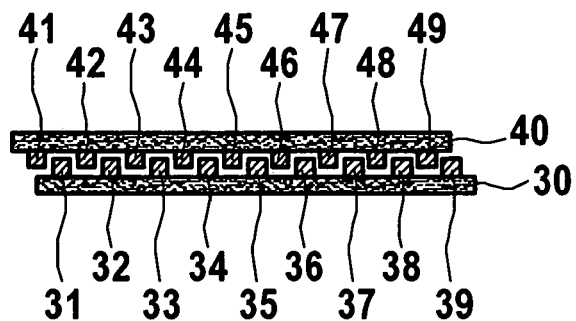
FIGS. 4a-4c illustrate a measuring principle for evaluating electrode materials, in which two substrates each including a plurality of electrode materials are moved in relation to each other.
Figure 4B:
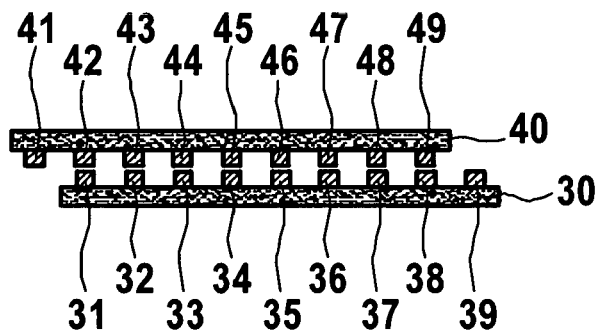
Figure 4C:
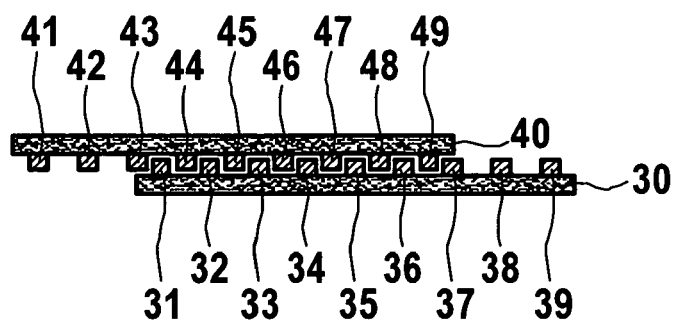

To determine an optimal electrode combination for the sensor, substrate 30 is arranged in a measuring vessel opposite a second substrate 40, which is also provided with nine different electrode materials 41 through 49, as is shown in FIGS. 4a through 4c. Substrate 40 and electrode materials 41 through 49 are used to develop a reference electrode from an optimized material.

To be able to test different electrode combinations in one medium, at least one of substrates 30 and 40 is provided with a motion device configured, for example, as a linear motor, via which substrates 30 and 40 may be displaced in relation to each other in such a manner that each of electrode materials 41 through 49 is arranged adjacent to each of electrode materials 31 through 39. A measurement of electrode material 31 in relation to electrode materials 41 and 42, and a measurement of electrode material 33 in relation to electrode materials 43 and 44, are possible, for example, in the representation shown in FIG. 4a. In the arrangement shown in FIG. 4c, electrode material 31 is measurable in relation to electrode materials 43 and 44, and electrode material 33 is measurable in relation to electrode materials 45 and 46. In FIG. 4b, the system is shown during the transfer of substrate 40 from one measuring arrangement to another.

To define the distance of substrate 30 to substrate 40 in measuring position, an electrically insulating plastic film is arranged on substrates 30 and 40 between electrode materials 31 through 39 and 41 through 49, respectively, the plastic film having a thickness of, for example, 150 mm. In measuring position, the electrode materials are in contact with the film areas of opposite substrate 30 and 40, respectively.

Figure 5:
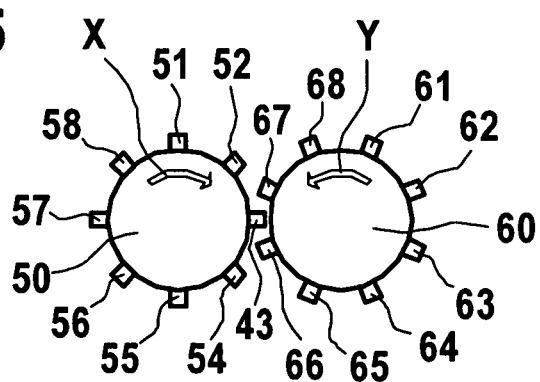
FIG. 5 shows two cylindrical substrates on which a plurality of electrode materials are arranged.

An exemplary embodiment of two substrates 50 and 60, which are movable in relation to each other, is shown in FIG. 5, each of substrates 50 and 60 being in the form of a cylinder and rotatable in relation to each other along direction arrows X and Y using an electric motor. Distributed over the perimeter of substrate 50 are eight electrode materials 51 through 58, each axially oriented and varying with respect to their chemical composition, electrode materials 51 through 58 being used for the development of a counter-electrode of an electrochemical sensor, and distributed over the perimeter of substrate 60 are eight electrode materials 61 through 68, which vary with respect to their chemical composition and are used for the development of a reference electrode of the electrochemical sensor, each forming a reference electrode in this case.

To determine the optimal electrode combination for a specific analyte, both substrates 50 and 60 are arranged in a measuring vessel containing the medium, which includes the analyte. The various electrode material combinations are then interconnected, cylindrical substrates being rotated into the corresponding measuring positions. In the position shown in FIG. 5, substrates 50 and 60 are arranged in such a manner that electrode material 43 arranged on the substrate 50 is measurable in relation to electrode materials 66 and 67 arranged on substrate 60. Rotating substrate 50 and/or substrate 60 makes it possible for all permutations of electrode combinations to be analyzed with respect to the delivered electrochemical potential.

What is claimed is:

1. A method, comprising:
   applying a plurality of different electrode materials to at least one substrate;
   introducing the plurality of different electrode materials into a medium together with at least one reference electrode;
   moving the at least one substrate in relation to the at least one reference electrode, thereby sequentially aligning each one of the plurality of different electrode materials with the at least one reference electrode; and
   determining an electrochemical potential of each one of the plurality of different electrode materials in relation to the at least one reference electrode.

2. The method of claim 1, wherein at least one of the plurality of different electrode materials is coated with an electrolyte.

3. The method of claim 1, wherein at least one of the plurality of different electrode materials and the at least one reference electrode are applied to the at least one substrate using a lithographic method.

4. The method of claim 1, wherein the at least one substrate is a cylindrical body.

5. The method of claim 4, wherein the at least one reference electrode is arranged on a second cylindrical body.

6. A system for optimizing a selection of a potentiometric electrode of an electrochemical measuring system, comprising:
   at least one substrate on which a plurality of different electrode materials are applied;
   at least one reference electrode;
   a measuring vessel in which the at least one substrate and the plurality of different electrode materials and the at least one reference electrode are positioned;
   at least one motion device for displacing the plurality of different electrode materials in relation to the at least one reference electrode, the at least one motion device configured to seguentially align each one of the plurality of different electrode materials with the at least one reference electrode; and
   a measuring device for measuring an electrochemical potential of each one of the plurality of different electrode materials in relation to the at least one reference electrode.

7. The system of claim 6, wherein at least one of the plurality of different electrode materials is coated with an electrolyte.

8. The system of claim 6, wherein leads for the plurality of different electrode materials are arranged on a side of the at least one substrate facing away from the plurality of different electrode materials.

9. The system of claim 6, further comprising:
   a reference substrate, wherein a plurality of different reference electrodes are arranged on the reference substrate.

10. The system of claim 6, wherein the at least one substrate is a cylindrical body.

11. The system of claim 10, wherein the at least one reference electrode is arranged on a second cylindrical body.

12. The system of claim 6, further comprising:
    a spacer that determines a spacing between the at least one reference electrode and the plurality of different electrode materials in measuring position.

* * * * *